United States Patent [19]

Rogosky

[11] Patent Number: 6,100,300

[45] Date of Patent: Aug. 8, 2000

[54] METFORMIN FORMULATIONS AND METHOD FOR TREATING INTERMITTENT CLAUDICATION EMPLOYING SAME

[75] Inventor: Karen M. Rogosky, Robbinsville, N.J.

[73] Assignee: Bristol-Myers Squibb Company, Princeton, N.J.

[21] Appl. No.: 09/067,565

[22] Filed: Apr. 28, 1998

[51] Int. Cl.[7] .................................................. A61K 31/155
[52] U.S. Cl. ............................................ 514/635; 564/233
[58] Field of Search .............................. 514/635; 564/233

[56] References Cited

PUBLICATIONS

Rouru et al. *Life Sciences* 1992, 50(23), 1813–1820.
Montanari, G., et al, "Treatment with Low Dose Metformin in Patients with Peripheral Vascular Disease", Pharmacological Research, vol. 25, No. 1, 1992, pp. 63–73.

Sirtori, C.R., et al, "Metformin Improves Peripheral Vascular Flow in Nonhyperlipidemic Patients with Arterial Disease", J. of Cardiovascular Pharmacology, vol. 6, No. 5, 1984, pp. 914–923.

*Primary Examiner*—Kathleen K. Fonda
*Attorney, Agent, or Firm*—Burton Rodney

[57] ABSTRACT

Novel metformin formulations are provided which include metformin or metformin salts preferably the hydrochloride salt in doses below that employed for treating diabetes such as metformin in daily amounts of 400 mg or below. A method for treating peripheral vascular disease including intermittent claudication employing such metformin formulations is also provided.

6 Claims, No Drawings

METFORMIN FORMULATIONS AND METHOD FOR TREATING INTERMITTENT CLAUDICATION EMPLOYING SAME

FIELD OF THE INVENTION

The present invention relates to novel metformin formulations which include metformin and salts thereof, preferably the hydrochloride salt, preferably in amounts below the threshold levels for treating diabetes, and to a method for treating peripheral vascular disease including intermittent claudication employing such metformin formulations.

BACKGROUND OF THE INVENTION

The biguanide antihyperglycemic agent metformin is concurrently marketed in the U.S. in the form of its hydrochloride salt (Glucophage™, Bristol-Myers Squibb Company).

The prior art is replete with references disclosing metformin salts of various organic or inorganic acids, for example, U.S. Pat. No. 3,174,901 discloses phosphate, sulfate, hydrobromide, salicylate, maleate, benzoate, succinate, ethanesulfonate, fumarate and glycolate salts of metformin;

U.S. Pat. No. 4,835,184 discloses the p-chlorophenoxyacetic acid salt of metformin;

French Patent Nos. 2320735 and 2037002 disclose the pamoate salt of metformin;

French Patent No. 2264539 and Japanese Patent No. 66008075 disclose the orotate salt of metformin;

French Patent No. 2275199 discloses the (4-chlorophenoxy)isobutyrate salt of metformin;

U.S. Pat. No. 4,080,472 discloses the clofibrate salt of metformin;

U.S. Pat. No. 3,957,853 discloses the acetylsalicylate salt of metformin;

French Patent No. 2220256 discloses the theophyllin-7-acetate salt of metformin;

German Patent Nos. 2357864 and 1967138 disclose the nicotinic acid salt of metformin;

U.S. Pat. No. 3,903,141 discloses the adamantoate salt of metformin;

Japanese Patent No. 69008566 discloses the zinc-chlorophyllin salt of metformin;

Japanese Patent No. 64008237 discloses hydroxy acid salts of metformin, including salts of hydroxy aliphatic dicarboxylic acids such as mesotartaric acid, tartaric acid, mesoxalic acids, and oxidized maleates;

Japanese Patent No. 63014942 discloses the tannic acid salt of metformin;

Japanese Patent Nos. 87005905 and 61022071 disclose the 3-methyl-pyrazole-5-carboxylic acid (or other 5-members hetercycle carboxylic acid) salt of metformin;

Romanian Patent No. 82052 discloses sulfamido aryloxyalkyl carboxylic acid salts of metformin;

Soviet Union Patent No. 992512 discloses the trimethoxy benzoic acid salt of metformin;

U.S. Pat. No. 4,028,402 discloses the dichloroacetic acid salt of metformin.

All of the above salts are formed of metformin: salt in a 1:1 molar ratio.

U.S. Pat. No. 5,631,224 to Efendic et al issued May 20, 1997, discloses a combination of metformin with GLP-1 (7–36) amide, or GLP-1(7–37) or a fragment thereof which retains GLP-1(7–37) activity.

Metformin has also been suggested for use in treating various cardiovascular diseases such as hypertension in insulin resistant patients (WO 9112003-Upjohn), for dissolving blood clots (in combination with a t-PA-derivative) (WO 9108763, WO 9108766, WO 9108767 and WO 9108765-Boehringer Mannheim), ischemia and tissue anoxia (EP 283369-Lipha), atherosclerosis (DE 1936274-Brunnengraber & Co., DE 2357875-Hurka, and U.S. Pat. No. 4,205,087-ICI). In addition, it has been suggested to use metformin in combination with prostaglandin-analogous cyclopentane derivatives as coronary dilators and for blood pressure lowering (U.S. Pat. No. 4,182,772-Hoechst). Metformin has also been suggested for use in cholesterol lowering when used in combination with 2-hydroxy-3,3,3-trifluoropropionic acid derivatives (U.S. Pat. No. 4,107,329-ICI), 1,2-diarylethylene derivatives (U.S. Pat. No. 4,061,772-Hoechst), substituted aryloxy-3,3,3-trifluoro-2-propionic acids, esters and salts (U.S. Pat. No. 4,055,595-ICI), substituted hydroxyphenyl-piperidones (U.S. Pat. No. 4,024,267-Hoechst), and partially hydrogenated 1H-indeno-[1,2B]-pyridine derivatives (U.S. Pat. No. 3,980,656-Hoechst).

Montanari et al, "Treatment With Lose Dose Metformin In Patients With Peripheral Vascular Disease", Pharmacological Research, Vol. 25, No. 1, 1992, discloses that use of metformin in amounts of 500 mg twice a day (b.i.d.) increased post-ischemia blood flow in a manner similar to 850 mg metformin three times a day (t.i.d.).

Sirtori et al, "Metformin Improves Peripheral Vascular Flow in Nonhyperlipidemic Patients with Arterial Disease", J. Cardiovas. Pharm., 6:914–923 (1984), discloses that metformin in amounts of 850 mg three times a day (t.i.d) increased arterial flow in patients with peripheral vascular disease.

DESCRIPTION OF THE INVENTION

In accordance with the present invention a novel metformin formulation is provided which includes a metformin or a salt thereof which will be included in an amount of less than about one-tenth (10%) of the dosage of metformin usually employed for treating diabetes, and preferably below the threshold level or dosage for treating diabetes.

In addition, in accordance with the present invention, a method is provided for treating peripheral vascular disease including intermittent claudication wherein a metformin formulation as described above is employed in therapeutically effective amounts to treat a mammalian species such as human, dogs, cats and the like. The amount of metformin salt employed will be less than about one-tenth (10%) of the dosage of metformin usually used for treating diabetes, and preferably below the threshold level or dosage for treating diabetes. Thus, daily amounts within the range from about 10 to about 400 mg, preferably from about 25 to about 200 mg, and more preferably from about 50 to about 150 mg may be employed.

The above dosages of metformin salt (in the formulation of the invention) may be administered in single or divided doses, one to three or more times a day.

The term "peripheral vascular disease" as employed herein refers to peripheral atherosclerotic disease also referred to as arteriosclerosis obliterans which involves occlusion of blood supply to the extremities by atherosclerotic plaques and encompasses intermittent claudication.

The term "intermittent claudication" as used herein refers to the pain that occurs in a muscle with an inadequate blood supply that is stressed by exercise (that is deficient blood supply in exercising muscle).

The metformin salt preferred for use herein will be the hydrochloride salt which is available under the tradename Glucophage® (Bristol-Myers Squibb Company). However other known salts may be employed in the formulation and method of the invention such as the phosphate, sulfate, hydrobromide, salicylate, maleate, benzoate, succinate, ethanesulfonate, fumarate and glycolate salts of metformin as disclosed in U.S. Pat. No. 3,174,901;

the p-chlorophenoxyacetic acid salt of metformin as disclosed in U.S. Pat. No. 4,835,184;

pamoate salt of metformin as disclosed in French Patent Nos. 2320735 and 2037002;

the orotate salt of metformin as disclosed in French Patent No. 2264539 and Japanese Patent No. 66008075;

the (4-chlorophenoxy)isobutyrate salt of metformin as disclosed in French Patent No. 2275199;

the clofibrate salt of metformin as disclosed in U.S. Pat. No. 4,080,472;

the acetylsalicylate salt of metformin as disclosed in U.S. Pat. No. 3,957,853;

the theophyllin-7-acetate salt of metformin as disclosed in French Patent No. 2220256;

nicotinic acid salt of metformin as disclosed in German Patent Nos. 2357864 and 1967138;

the adamantoate salt of metformin as disclosed in U.S. Pat. No. 3,903,141;

the zinc-chlorophyllin salt of metformin as disclosed in Japanese Patent No. 69008566;

hydroxy acid salts of metformin, including salts of hydroxy aliphatic dicarboxylic acids such as mesotartaric acid, tartaric acid, mesoxalic acids, and oxidized maleates as disclosed in Japanese Patent No. 64008237;

the tannic acid salt of metformin as disclosed in Japanese Patent No. 63014942;

the 3-methyl-pyrazole-5-carboxylic acid (or other 5-members hetercycle carboxylic acid) salt of metformin as disclosed in Japanese Patent Nos. 87005905 and 61022071;

the aryloxyalkyl carboxylic acid salts of metformin as disclosed in Romanian Patent No. 82052;

the trimethoxy benzoic acid salt of metformin as disclosed in Soviet Union Patent No. 992512;

the dichloroacetic acid salt of metformin as disclosed in U.S. Pat. No. 4,028,402.

Surprisingly, it has been found that metformin or salts thereof may be employed in amounts of 10% or less of that required to effect glucose lowering in diabetics, and preferably in amounts below that required to treat diabetes, and will be useful in treating peripheral vascular disease.

The metformin formulation of the present invention can be administered to various mammalian species, such as dogs, cats, humans, etc., for use in treating intermittent claudication or other peripheral vascular diseases. These metformin salts can be administered systemically, preferably orally.

The metformin salts can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms of the metformin (2:1) salt of the invention described above may be administered in amounts less than about 10% of amounts as described for metformin hydrochloride (Bristol-Myers Squibb Company's Glucophage®) as set out in the Physician's Desk Reference.

The formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tablet disintegrants in an amount within the range of from about 0.5 to about 10% and preferably from about 2 to about 8% by weight of the composition such as croscarmellose sodium, povidone, crospovidone, sodium starch glycolate, corn starch or microcrystalline cellulose as well as one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer which is applied over the tablet core may comprise any conventional coating formulations and will include one or more film-formers or binders, such as a hydrophilic polymer like hydroxypropylmethyl cellulose and a hydrophobic polymer like ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

A preferred tablet composition of the invention will include from about 5 to about 95% by weight metformin HCl salt from about 2 to about 8% by weight providone, from about 4 to about 15% by weight hydropropyl methylcellulose, and from about 0.5 to about 2% by weight magnesium stearate.

The pharmaceutical composition of the invention may be prepared as follows. A mixture of the medicament and a fraction (less than 50%) of the filler where present (such as lactose), with or without color, are mixed together and passed through a #12 to #40 mesh screen. Filler-binder where present (such as microcrystalline cellulose), disintegrant (such as providone) are added and mixed. Lubricant (such as magnesium stearate) is added with mixing until a homogeneous mixture is obtained.

The resulting mixture may then be compressed into tablets of up to 2 grams in size.

Where desired, the tablets of the invention may be formulated by a wet granulation techniques as disclosed in U.S. Pat. No. 5,030,447 which is incorporated herein by reference.

The following examples represent preferred embodiments of the invention.

EXAMPLE 1

Preparation of Tablets Containing Metformin HCl Salt

Tablets of the following formulation were prepared as described below.

| Ingredient | Amount per tablet (mg) |
| --- | --- |
| Metformin HCl salt | 50 mg |
| Microcrystalline cellulose NF | 8 mg |
| Croscarmellose sodium NF | 4.5 mg |
| Povidone USP | 1.5 mg |
| Magnesium Stearate NF | 0.8 mg |

In a planetary mixer metformin salt was blended with half the microcrystalline cellulose and with the croscarmellose sodium. The povidone USP was dissolved in a suitable quantity of purified water and this solution was used to wet granulate the drug-excipient mixture. The granules were dried in an oven at 60° C. to a moisture content of 1.5–2.5% w/w. In a V-cone blender the granules were mixed with the remaining microcrystalline cellulose and then with the magnesium stearate. The resulting mix was compressed into tablets using suitable capsule shaped tooling. The so-formed metforin salt tablets are useful in treating peripheral vascular disease including intermittent claudication.

EXAMPLE 2

Preparation of Tablets Containing Metformin HCl Salt

Tablets of the following formulation may be prepared employing conventional formulating techniques.

| Ingredient | Amount per tablet (mg) |
| --- | --- |
| Metformin HCl salt | 50 mg |
| Povidone | 4.5 mg |
| Hydroxypropylmethyl cellulose (5 cps) (HPMC) USP | 15.0 mg |
| Magnesium Stearate NF | 0.8 mg |

For example, tablets may be prepared as follows.

In a planetary mixer metformin salt is blended with half the hydroxypropylmethyl cellulose. The povidone USP is dissolved in a suitable quantity of purified water and this solution is used to wet granulate the drug-excipient mixture. The granules are dried in an oven at 60° C. to a moisture content of 1.5–2.5% w/w. In a V-cone blender the granules are mixed with the remaining hydroxypropylmethyl cellulose and then with the magnesium stearate. The resulting mix is compressed into tablets using suitable capsule shaped tooling.

The so-formed metformin salt tablets are useful in treating peripheral vascular disease including intermittent claudication.

What is claimed is:

1. A method for treating peripheral vascular disease which comprises administering to a human patient in need of such treatment a therapeutically effective amount of metformin or a salt thereof in an amount within the ranae from about 10 to about 400 mg per day.

2. The method as defined in claim 1 wherein the metformin in the form of the HCl salt is administered.

3. The method as defined in claim 1 wherein the metformin in the form of the HCl salt is administered in single or divided dosages one to three times daily.

4. The method as defined in claim 1 wherein the metformin in the form of the HCl salt is administered in a daily dosage within the range from about 25 to about 200 mg per day in single or divided dosages one to three times daily.

5. The method as defined in claim 1 wherein the metformin in the form of the HCl salt is administered in a daily dosage within the range from about 50 to about 150 mg per day in single or divided dosages one to three times daily.

6. The method as defined in claim 1 for treating intermittent claudication.

* * * * *